United States Patent
Holman

(10) Patent No.: US 6,277,875 B1
(45) Date of Patent: Aug. 21, 2001

(54) USE OF DOPAMINE $D_2/D_3$ RECEPTOR AGONISTS TO TREAT FIBROMYALGIA

(76) Inventor: Andrew J. Holman, 19658 Marine View Dr., SW., Seattle, WA (US) 98166

(*) Notice: Subject to any disclaimer, the term of this patent is extended or adjusted under 35 U.S.C. 154(b) by 0 days.

(21) Appl. No.: 09/617,177

(22) Filed: Jul. 17, 2000

(51) Int. Cl.⁷ ............................. A61K 3/425; A61K 31/40
(52) U.S. Cl. ........................... 514/367; 514/418; 514/421
(58) Field of Search .................................. 514/367, 418, 514/421

(56) References Cited

U.S. PATENT DOCUMENTS

| | | |
|---|---|---|
| 5,658,955 | 8/1997 | Hitzig . |
| 5,696,128 | 12/1997 | Cincotta et al. . |
| 5,872,127 | 2/1999 | Cincotta et al. . |
| 5,872,133 | 2/1999 | Cincotta et al. . |
| 5,905,083 | 5/1999 | Cincotta et al. . |

OTHER PUBLICATIONS

"Pramipexole—a new dopamine agonist for the treatment of Parkinson's disease", Bennett et al., 1999, J. Neurol. Sci.; Abstract.*

"Electrophysiologic testing in Parkinson's disease", Arora et al., 1999, Am J. Electoneurodiagnostic Tech.; Abstract.*

"Cerebrospinal fluid biogenic amine metabolites in fibromyalgia/fibrositis syndrome and rheumatoid arthritis", Russell et al., 1992, Arthritis and Rheumatism; Abstract.*

Harvey Moldofsky, MD, et al., "Induction of Neurasthenic Musculoskeletal Pain Syndrome by Selective Sleep Stage Deprivation," *Psychosomatic Medicine*, vol. 38, No. 1 (Jan.–Feb. 1976), pp. 35–44.

Harvey Moldofsky, "Sleep Influences on Regional and Diffuse Pain Syndromes Associated with Osteoarthritis," *Seminars in Arthritis and Rheumatism*, vol. 18, No. 4, Suppl 2 (May), 1989, pp. 18–21.

J.G.MacFarlane et al., "Period K–Alpha Sleep EEG Activity and Periodic Limb Movements During Sleep: Comparisons of Clinical Features and Sleep Parameters," *Sleep*, vol. 19, No. 3 (1996), pp. 200–204.

Muhammad B. Yunus et al., "Restless legs syndrome and leg cramps in fibromyalgia syndrome: a controlled study," *BMF*, 1996, vol. 312, p. 1339.

Mark H. Corrigan, M.D. et al., "Comparison of Pramipexole, Fluoxetine, and Placebo in Patients with Major Depression," *Depression and Anxiety*, vol. 11, pp. 58–65 (2000).

Manuel Martinez–Lavin et al., "Circadian Studies of Autonomic Nervous Balance in Patients with Fibromyalgia—A Heart Rate Variability Analysis," *Arthritis & Rheumatism*, vol. 41, No. 11, Nov. 1998, pp. 1966–1971.

Stanley R. Pillemer et al., "The Neuroscience and Endocrinolgy of Fibromyalgia," *Arthritis & Rheumatism*, vol. 40, No. 11, Nov. 1997, pp. 1928–1939.

Andrew J. Holman, Abstract 487, "Safety and Efficacy of Lorazepam for Refractory Fibromyalgia After One Year."

Jonathan Sporn, M.D., et al., "Pramipezole Augmentation in the Treatment of Unipolar and Bipolar Depression: A Retrospective Chart Review," *Annals of Clinical Psychiatry*, vol. 12, No. 3, 2000.

Gary W. Jay, MD, DAAPM, et al., "Fibromyalgia Syndrome,"Current Trends in the Diagnosis and Treatment of Chronic Neuromuscular Pain Syndromes, Educational Program Sponsored by the American Academy of Pain Mangement, Released Aug. 2000.

* cited by examiner

*Primary Examiner*—Zohreh Fay
*Assistant Examiner*—Brian-Yong Kwon
(74) *Attorney, Agent, or Firm*—Christensen O'Connor Johnson Kindness PLLC

(57) ABSTRACT

The present invention is directed to metho s for the treatment of human patients afflicted with fibromyalgia using a nonergot dopamine receptor D2/D3 agonist. In particular, patients are treated with a therapeutically effective amount of tetrahydro-benzthiazole or 3(H)-indolone compounds that are dopamine agonists. More specifically, the compounds 2-amino-6-n-propylamino-4,5,6,7-tetrahydrobenzo-thiazole or 4-[2-(dipropylamino)-ethyl]-1,3-dihydro-2H-indol-2-one are administered to fibromyalgia patients to reduce the musculoskeletal pain symptoms associated with fibromyalgia.

5 Claims, No Drawings

USE OF DOPAMINE $D_2/D_3$ RECEPTOR AGONISTS TO TREAT FIBROMYALGIA

FIELD OF THE INVENTION

The present invention relates to methods for the treatment of fibromyalgia using non-ergot dopamine $D_2/D_3$ agonists. More specifically, tetrahydro-benzthiazoles, in particular, 2-amino-6-n-propylamino-4,5,6,7-tetrahydrobenzo-thiazole or the (-)-enantiomers thereof, and certain 3(H)-indolone derivatives, in particular, 4-[2-(dipropylamino)-ethyl]-1,3-dihydro-2H-indol-2-one, and the pharmacologically acceptable salts thereof, alone or in association with a pharmaceutically acceptable carrier, can be used to treat fibromyalgia patients.

BACKGROUND OF THE INVENTION

Fibromyalgia is a common disabling disorder characterized by chronic musculoskeletal aches and pain, stiffness, general fatigue, and sleep abnormalities including diminished stage four sleep. Fibromyalgia is a chronic, painful disorder commonly seen in rheumatology practice and is often viewed as a musculoskeletal pain process. Fibromyalgia is characterized as a reproducible, neurosensory processing abnormality associated with fatigue, and generalized muscular spasm, which most rheumatologists suspect is related to stage IV sleep deprivation. Examination of affected patients reveals increased tenderness at muscle and tendon insertion sites, known as "tender points". Fibromyalgia patients experience severe morning stiffness and a generalized decreased of overall physical function, and they are often prone to headaches, memory and concentration problems, dizziness, numbness and tingling, and crampy abdominal or pelvic pain. Fibromyalgia affects 2–4% of the population and is most frequently found in women between 20 and 50 years old, though it can also affect men, the elderly and minors.

Diagnosis of fibromyalgia is often overlooked due to the general nature of the symptoms and the lack of diagnostic lab or x-ray abnormalities. The disorder is often concomitant with, masked by or confused with other diseases such as rheumatoid arthritis, chronic fatigue syndrome or irritable bowl syndrome. A physician can positively diagnose fibromyalgia syndrome by finding the symptoms of generalized musculoskeletal pain and pain at more than 11 of 18 defined characteristic "tender points" when finger pressure of about 4 kg is applied to the area. The total pain score for all 18 tender points is referred to as the "tender point index" of that patient. The efficacy of a particular fibromyalgia therapy is demonstrated by a observation of a statistically significant improvement in a patient's tender point index.

The etiology of fibromyalgia is not known but consideration has been given to genetic, traumatic, affective, and infectious processes as possibilities. Currently the best treatment available for fibromyalgia consists of a combination of analgesics, sleep aids, exercise programs emphasizing stretching and cardiovascular fitness, relaxation techniques and other measures to reduce muscle tension, and educational and psychological support programs to reduce emotional and physical stress; the resulting benefits are usually disappointing. Numerous pharmaceutical regimes have been tried including treatment with serotonin modulators and antisera to endogenous psychoactive agents. Therapeutic response can be assessed by the reduction of pain in the tender point index and improvement in several generalized criteria such as physical function, stiffness, fatigue, depression, tenseness, etc. Responses to these various therapies have proven variable within a patient pool and have rarely exceeded modest relief of some symptoms.

For example, Hitzig (U.S. Pat. No. 5,658,955) discloses the treatment of a broad range of immune disorders, including fibromyalgia, with an effective amount of a serotonin agonist and a dopamine agonist. The preferred dopamine agonist discussed in Hitzig is phentermine which is an adrenergic compound. Further, none of the dopamine agonists cited in Hitzig are non-ergot dopamine receptor $D_2/D_3$ agonists. Hitzig also includes no data in support of their statement that fibromyalgia can be treated with a serotonin agonist and a dopamine agonist. Also, fibromyalgia is no longer thought of as an autoimmune disorder, indeed the clinical name associated with the disease was changed from fibrositis to fibromyalgia to specifically remove any connotation of an immune or inflammatory condition.

Cincotta et al. (U.S. Pat. Nos. 5,905,083, 5,872,133, 5,872,127, and 5,696,128) also discloses the use of a serotonin agonist and a dopamine agonist at particular times of the day to treat a wide variety of immune disorders. More specifically they suggest that a variety of immune disorders can be treated by providing patients with an amount of the serotonin and dopamine agonists sufficient to adjust the prolactin profile of the patient. The Cincotta et al. patents list fibromyalgia as one of the many immune disorders that can be treated by prolactin management. However, other clinical studies have not validated the association between prolactin and fibromyalgia (Alder et al., Am. J. Med. 106:534–543 (1999); Griep et al., J. Rheumatol. 21:2125–2130 (1994)).

U.S. Patent Serial No. 6,036,949 discloses that low doses of interferon can be used to treat fibromyalgia. However, the clinical study disclosed in the patent showed only a modest improvement in the severity of morning stiffness, one of the secondary symptoms of fibromyalgia. The pressure point pain index for fibromyalgia patients receiving interferon did not show any statistically significant improvement relative to a placebo group.

In the past, there was a tendency to view fibromyalgia as a benign disorder which did not justify aggressive therapy which might carry with it any risk of adverse experience. However, that philosophy can no longer be justified considering the impact of this condition on the quality of life of affected individuals. Considering that the annual direct cost of fibromyalgia to the United States economy is estimated at $16 billion, there exists a significant need for more effective therapy for patients afflicted with fibromyalgia.

The tetrahydro-benzthiazoles useful in the present invention, are dopamine-$D_2/D_3$ agonists the syntheses of which are described in European Patent 186 087 and its counterparts, U.S. Pat. Nos. 4,843,086 and 4,886,812. These compounds are known primarily for the treatment of schizophrenia and Parkinson's disease. It is known from German patent application DE 38 43 227 that 2-amino-6-n-propylamino-4,5,6,7-tetrahydrobenzo-thiazole (pramipexole) can be used in the treatment of drug dependency. Further, it is known from German patent application DE 39 33 738 that pramipexole can be used to decrease abnormal high levels of thyroid stimulating hormone (TSH). U.S. Pat. No. 5,112,842 discloses the transdermal administration of the compounds and transdermal systems containing these active compounds. The WO patent application PCT/EP 93/03389 describes pramipexole as an antidepressant agent, while U.S. Pat. No. 5,650,420 discloses the neuroprotective effects of pramipexole. U.S. Pat. No. 6,001,861 discloses the use of pramipexole in the treatment of restless legs syndrome.

Similarly, the indolone compounds, useful in the present invention, are also dopamine receptor $D_2/D_3$ agonists, the syntheses of which are described in U.S. Pat. No. 4,452,808. U.S. Pat Nos. 4,912,126 and 4,824,860 further disclose that these indolone compounds, in particular, 4-[2-(dipropylamino)-ethyl]-1,3-dihydro-2H-indol-2-one, can be used to treat Parkinson's disease.

Dopamine receptor $D_2/D_3$ agonists have been reported as not being capable of producing the central behavioral effects often seen with other classes of dopamine agonists (see Gallagher et al., *J. Med. Chem.* 28:1533–1536 (1985)). Furthermore, it has been reported that $D_2/D_3$ agonists show minimal liability to cause dyskinesia. Dyskinesia is a common problem associated with postsynaptic dopamine agonists, for example ergo alkaloids such as bromocriptine.

The present invention is directed to a method for treating the disease condition (as measured by reduction of clinical symptoms) by treating a fibromyalgia afflicted patient with a non-ergot dopamine receptor $D_2/D_3$ agonist and the pharmacologically acceptable salts thereof.

SUMMARY OF THE INVENTION

The present invention provides a method for treating patients suffering from fibromyalgia are treated with an effective amount of a non-ergot dopamine receptor $D_2/D_3$ receptor agonist.

In one embodiment of the invention, a patient suffering from fibromyalgia is treated with an affective amount of a tetrahydro-benzthiazole compound of the following formula I:

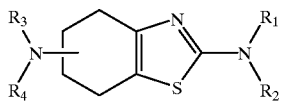

(I)

wherein
- $R_1$ represents a hydrogen atom, a $C_{1-6}$ alkyl group, a $C_{3-6}$ alkenyl, a $C_{3-6}$ alkynyl group, a $C_{1-6}$ alkanoyl group, a phenyl $C_{1-3}$ alkyl group, or a phenyl $C_{1-3}$ alkanoyl group, the phenyl nuclei may be substituted by 1 or 2 halogen atoms;
- $R_2$ represents a hydrogen atom or a $C_{1-4}$ alkyl group;
- $R_3$ represents a hydrogen atom, a $C_{1-7}$ alkyl group, a $C_{3-7}$ cycloalkyl group, a $C_{1-3}$ alkenyl, $C_{1-3}$ alkynyl group, a $C_{1-7}$ alkanoyl group, a phenyl $C_{1-3}$ alkyl, or a phenyl $C_{1-3}$ alkanoyl group, the phenyl nuclei may be substituted by fluorine, chlorine or bromine atoms;
- $R_4$ represents a hydrogen atom, a $C_{1-4}$ alkyl group, a $C_{3-6}$ alkenyl, or a $C_{3-6}$ alkynyl group, or $R_3$ and $R_4$ together with the nitrogen atom between them represent a pyrrolidino, piperidino, hexamethyleneimino or morpholino group, and the pharmacologically acceptable acid addition salts thereof, alone or in association with a pharmaceutically acceptable carrier.

In another aspect of the invention, fibromyalgia is treated by administering to a subject in need thereof an effective amount of a compound of formula II:

wherein $R_1$ is hydrogen or $C_{1-4}$ alkyl; $R_2$ and $R_3$ are each independently

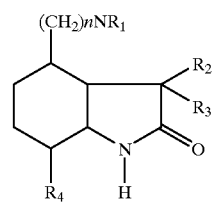

(II)

hydrogen or $C_{1-4}$ alkyl; $R_4$ is hydrogen or hydroxy; and n is 1 to 3; or a pharmaceutically acceptable salt thereof.

This and other aspects of the invention will be apparent from the description of the invention which follows below.

DETAILED DESCRIPTION OF THE PREFERRED EMBODIMENT

In accordance with the present invention, methods are provided for the treatment of fibromyalgia. Thus, in one aspect the present invention provides a method of inhibiting the symptoms of fibromyalgia comprising administering to a patient in need of such treatment an effective amount of a non-ergot $D_2/D_3$ receptor agonist or a pharmaceutically acceptable acid addition salts thereof; either alone or together with a pharmaceutically acceptable carrier.

In another aspect of the invention, the dopamine $D_2/D_3$ receptor agonist used to treat fibromyalgia is selected from the group consisting of:

(a) a tetrahydro-benzthiazole compound of formula (I):

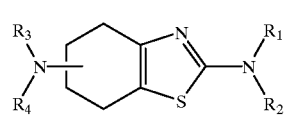

(I)

wherein
- $R_1$ represents a hydrogen atom, a $C_{1-6}$ alkyl group, a $C_{3-6}$ alkenyl, a $C_{3-6}$ alkynyl group, a $C_{1-6}$ alkanoyl group, a phenyl $C_{1-3}$ alkyl group, or a phenyl $C_{1-3}$ alkanoyl group, the phenyl nuclei may be substituted by 1 or 2 halogen atoms;
- $R_2$ represents a hydrogen atom or a $C_{1-4}$ alkyl group;
- $R_3$ represents a hydrogen atom, a $C_{1-7}$ alkyl group, a $C_{3-7}$ cycloalkyl group, a $C_{1-3}$ alkenyl, $C_{1-3}$ alkynyl group, a $C_{1-7}$ alkanoyl group, a phenyl $C_{1-3}$ alkyl, or a phenyl $C_{1-3}$ alkanoyl group, the phenyl nuclei may be substituted by fluorine, chlorine or bromine atoms;
- $R_4$ represents a hydrogen atom, a $C_{1-4}$ alkyl group, a $C_{3-6}$ alkenyl, or a $C_{3-6}$ alkynyl group, or $R_3$ and $R_4$ together with the nitrogen atom between them represent a pyrrolidino, piperidino, hexamethyleneimino or morpholino group, and the pharmacologically acceptable acid addition salts thereof, alone or in association with a pharmaceutically acceptable carrier.

(b) 3(H)-indolone compound of formula (II):
wherein

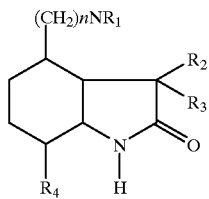

(II)

$R_1$ is hydrogen or $C_{1-4}$ alkyl;
$R_2$ and $R_3$ are each hydrogen or $C_{1-4}$ alkyl;
$R_4$ is hydrogen or hydroxy; and
n is 1 to 3, and (c) any combination thereof.

In some embodiments of the invention the compounds of formula (I) and (II) above may be formulated as a pharmaceutically acceptable salt and further include a pharmaceutically acceptable carrier.

Preferred tetrahydro-benzthiazole compounds of general formula (I) above are those wherein the group is in the 5 or 6-position.

As examples of the definitions of the groups

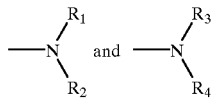

group represents an amino, methylamino, ethylamino, n-propylamino,

isopropylamino, n-butylamino, isobutylamino, tert-butylamino, n-pentylamino, isoamylamino, n-hexylamino, dimethylamino, diethylamino, di-n-propylamino, di-n-butylamino, methyl-ethylamino, methyl-n-propylamino, methyl-isopropylamino, ethyl-isopropylamino, allylamino, buten-2-ylamino, hexen-2-ylamino, N-methyl-allylamino, N-ethyl-allylamino, N-n-propyl-allylamino, N-n-butyl-allylamino, propargylamino, N-methyl-propargylamino, N-n-propyl-propargylamino, formylamino, acetylamino, propionylamino, butanoylamino, hexanoylamino, N-methyl-acetylamino, N-allyl-acetylamino, N-propargyl-acetylamino, benzylamino, N-methyl-benzylamino, 2-chloro-benzylamino, 4-chloro-benzylamino, 4-fluoro-benzylamino, 3,4-dichloro-benzylamino, 1-phenylethylamino, 2-phenylethylamino, 3-phenyl-n-propylamino, benzoylamino phenacetylamino or 2-phenylpropionylamino group and

may represent an amino, methylamino, ethylamino, n-propylamino, isopropylamino, n-butylamino, isobutylamino, tert-butylamino, n-pentylamino, isoamylamino, n-hexylaamino, n-heptylamino, dimethylamino, diethylamino, di-n-propylamino, Di-n-butylamino, methyl-ethylamino, methyl-n-propylamino, methyl-isopropylamino, ethyl-isopropylamino, allylamino, buten-2-ylamino, hexen-2-ylamino, diallylamino, N-methyl-allylamino, N-ethyl-allylamino, N-n-propyl-allylamino, N-n-butyl-allylamino, propargylamino, butin-2-ylamino, hexin-2-ylamino, dipropargylamino, N-methyl-propargylamino, N-ethyl-propargylamino, cyclopropylamino, cyclobutylamino, cyclopentylamino, cyclohexylamino, cycloheptylamino, N-methyl cyclohexylamino, N-ethyl-cyclohexylamino, formylamino, acetylamino, propionylamino, butanoylamino, pentanoylamino, hexanoylamino, heptanoylamino, N-methyl-acetylamino, N-ethyl-acetylamino, N-n-propyl-acetylamino, N-allyl-acetylamino, benzoylamino, fluorobenzoylamino, chlorobenzoylamino, bromobenzoylamino, phenylacetamino, 2-phenylpropionylamino, N-methyl-benzoylamino, N-ethyl-chlorobenzoylamino, dichlorobenzoylamino, N-cyclohexyl-acetylamino, benzylamino, chlorobenzylamino, bromobenzylamino, 1-phenylethylamino, 2-phenylethylamino, 2-phenyl-n-propylamino, 3-phenyl-n-propylamino, N-methyl-benzylamino, N-ethyl-benzylamino, N-ethyl-chlorobenzylamino, N-ethyl-2-phenylethylamino, N-acetyl-benzylamino, N-acetyl-chlorobenzylamino, N-allyl-benzylamino, N-allyl-chlorobenzylamino, pyrrolidino, piperidino, hexamethyleneimino or morpholino group.

Particularly preferred compounds of general formula (I) are, however, the compounds of general formula (Ia)

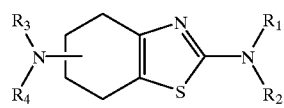

(Ia)

wherein
$R_1$ represents a hydrogen atom, an alkyl group having 1 to 3 carbon atoms, an allyl, benzyl, 2-chloro-benzyl, 4-chloro-benzyl, 3,4-dichloro-benzyl or phenylethyl group.

$R_2$ represents a hydrogen atom, a methyl or ethyl group, $R_3$ represents a hydrogen atom, an alkyl group with 1 to 6 carbon atoms, an allyl, propargyl, benzyl, chlorobenzyl, phenylethyl, cyclopentyl or cyclohexyl group, $R_4$ represents a hydrogen atom, an alkyl group having 1 to 3 carbon atoms or an allyl group or $R_3$ and $R_4$ together with the nitrogen atom between them represent a pyrrolidino, piperidino, hexamethylene-imino or morpholino group, but particularly the compounds wherein the group is in the 6-position, and the acid addition salts thereof, particularly the

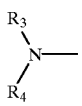

pharmaceutically acceptable acid addition salts; either alone or together with a pharmaceutically acceptable carrier.

More particularly preferred compounds for use in the present invention are of general formula (Ia) are, however, the compounds of general formula (Ib)

wherein

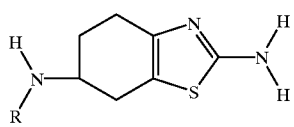

(Ib)

R is a hydrogen atom, a $C_{1-7}$ alkyl group, a $C_{3-7}$ cycloalkyl group, a $C_{3-6}$ alkenyl, $C_{3-6}$ alkynyl group, or a phenyl $C_{1-3}$ alkyl group, wherein the phenyl nucleus may be substituted by fluorine, chlorine or bromine atoms; or, a pharmaceutically acceptable acid addition salt thereof.

Preferred compounds of general formula (II) above are those wherein the group $R_1$ is $C_{1-4}$ alkyl, in particular, propyl, $R_2$ and $R_3$ are both hydrogen, and $R_4$ is hydrogen or hydroxy.

In particular, preferred 3(H)-indolone compounds for use in the method of the present invention include the compound of structure (II) above in which $R_1$ is propyl, $R_2$, $R_3$ and $R_4$ are hydrogen and n is 2, namely the compound 4-[2-(dipropylamino)-ethyl]-1,3-dihydro-2H-indol-2-one or a pharmaceutically acceptable salt thereof. Suitable salts will be apparent to those skilled in the art and include, for example acid addition salts, preferably the hydrochloride.

The synthesis, formulation and administration of the tetrahydro-benzthiazole compounds of formula (I) that are used in the practice of the present invention are described in U.S. Pat. Nos. 4,843,086; 4,886,812; 5,112,842; 5,650,420 and 6,001,861, which are incorporated by reference herein. The compounds of general formula (I) have at least one chiral center and can, therefore, exist in the form of various stereoisomers. The invention embraces all of these stereoisomers and mixtures thereof. Mixtures of these stereoisomers can be resolved by conventional methods, e.g. by column chromatography on a chiral phase, by fractional crystallization of the diastereomeric salts or by column chromatography of their conjugates with optically active auxiliary acids such as tartaric acid, O,O-dibenzoyl-tartaric acid, camphor acid, camphorsulfonic acid or α-methoxyphenylacetic acid.

The synthesis, formulation and administration of the 3(H)-indolone compounds of formula (II) above that are used in the practice of the present invention is described in U.S. Pat. Nos. 4,452,808.

The compounds of formula (I) and (II) may also be converted into the acid addition salts thereof, particularly the pharmaceutically acceptable acid addition salts with inorganic or organic acids. Suitable acids for this include, for example, hydrochloric, hydrobromic, sulfuric, phosphoric, lactic, citric, tartaric, succinic, maleic or fumaric acid.

In another aspect of the invention, a patient is first determined to be suffering from fibromyalgia based upon the occurrence of musculoskeletal pain symptoms, and then the patient is treated by administering an effective amount of a dopamine $D_2/D_3$ receptor agonist, preferably, one of the compounds of general formula (I) and (II) to modulate the pain symptoms of fibromyalgia, as set forth herein.

A physician can positively diagnosis fibromyalgia by finding the symptoms of generalized musculoskeletal pain at more than 11 of 18 defined characteristic "tender points" when finger pressure of about 4 kg is applied to the area, which test is known as the "tender point index". As used herein the term "musculoskeletal pain" refers to pain associated with one or more of the 18 defined "tender points" commonly surveyed in the diagnosis of fibromyalgia. The "tender points" survey is well known in the art, see for example, Wolfe et al.(*Arthritis and Rheumatism*, 33:160–172, 1990).

The tetrahydro-benzthiazole compounds of formula (I), (Ia) and (Ib), particularly the (-)-entantiomers thereof, and 3(H)-indolones of formula (II) and pharmacologically acceptable acid addition salts thereof, alone or in combination with a pharmaceutical carrier can be used to treat fibromyalgia. The form of conventional galenic preparations consist essentially of an inert pharmaceutical carrier and an effective dose of the active substance; e.g., plain or coated tablets, capsules, lozenges, powders, solutions, suspensions, emulsions, syrups, suppositories, inhaler, transdermal patches etc.

The term "effective amount" as used herein means an amount of a compound of the invention effective to result in the clinically determinable improvement in or suppression of symptoms of fibromyalgia, such as musculoskeletal pain. An improvement in such symptoms includes both a reduction in intensity and frequency of musculoskeletal pain and a complete cessation of musculoskeletal pain for a sustained period. Typically effective amounts of the compounds of the invention will generally range from about 0.1 mg/day to about 50 mg/day, more preferably about 0.25 mg/day to about 40 mg/day and most preferably about 0.5 mg/day to about 20 mg/day.

More preferably, the patient is administered an effective amount of 2-amino-6-n-propylamino-4,5,6,7-tetrahydrobenzo-thiazole or the (-)-enantiomers thereof, and the pharmacologically acceptable salts thereof, alone or in association with a pharmaceutically acceptable carrier. Alternatively, the patient is administered an effective amount of 4-[2-(dipropylamino)-ethyl]-1,3-dihydro-2H-indol-2-one and the pharmacologically acceptable salts thereof, alone or in association with a pharmaceutically acceptable carrier.

In a presently particularly preferred embodiment of the invention, a patient suffering from fibromyalgia is administered pramipexole which is a particular pharmaceutical formulation of (S)-2-amino-4,5,6,7-tetrahydro-6-(propylamino)benzo-thiazole dihydrochloride monohydrate available from Pharmacia & Upjohn under the trademark MIRAPEX® (Physicians' Desk Reference, $53_{rd}$ edition, 2497-2501, 1999, Medical Economics Co., Inc. Montvale, N.J.).

In a second particularly preferred embodiment of the invention, a patient suffering from fibromyalgia is administered ropinirole which is a particular pharmaceutical formulation of 4-[2-(dipropylamino)-ethyl]-1,3-dihydro-2H-indol-2-one available from Smith Kline Beecham under the trademark Requip® (Physicians' Desk Reference, $53_{rd}$ edition, 3087–3092, 1999, Medical Economics Co., Inc. Montvale, N.J.).

The compounds of the present invention can be used in the form of salts derived from inorganic or organic acids.

These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I) and (II), or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds may be used alone or in compositions together with a pharmaceutically acceptable carrier. In addition, the dopamine agonist used in the practice of the present invention can be used in combination with a variety of other pharmaceutical compositions. For example, in the practice of the inventive fibromyalgia treatment method it is common to use the dopamine agonists in combination with Ativan® (Wyeth-Ayerst Laboratories (Philadelphia, Pa.), an antianxiety agent, or Klonopin® (Roche Laboratories, Nutley, N.J.), an antipanic agent, to control sympathetic tone, and to add an option for stage III/IV sleep control such as Trazodone, a muscle relaxant or melatonin. Initially, many fibromyalgia patients are undergoing treatment with Sinemet®, which is commonly used to treat fibromyalgia. Patients are counseled to discontinue Sinemet®, and to decrease any somnolent medications as the dopamine receptor $D_2/D_3$ agonist treatment regime become effective.

Patients are initially treated with the dopamine receptor $D_2/D_3$ agonist at the low end of the recommended dose, for example, in the case of prarnipexole (2-amino-6-n-propylamino-4,5,6,7 tetrahydrobenzothiozole) a dose of about 0.125 mg once per day at bedtime (qhs), and in the case of ropinirole (4-[2-(dipropylamino)-ethyl]-1,3-dihydro-2H-indol-2-one), a patient starts at 0.25 mg qhs.

The standard dose regime for treatment of fibromyalgia with the dopamine receptor $D_2/D_3$ agonists then involves increasing the amount of agonists gradually on weekly basis until the patient exhibits an therapeutic effect or intolerance (see Table 1). Alternatively, if desired, a more rapid dosage regime may also be used (see Table 1).

TABLE 1

Two possible dopamine receptor $D_2/D_3$ dosing regimes.

| | Standard Dosing | | | Rapid Dosing | |
| --- | --- | --- | --- | --- | --- |
| | Dose (mg qhs) | | | Dose (mg qhs) | |
| Week | Pramipexole | Ropinirole | Week | Pramipexole | Ropinirole |
| 1 | 0.125 | 0.25 | 1 | 0.5 | 0.25 |
| 2 | 0.25 | 0.5 | 2 | 1.0 | 0.5 |
| 3 | 0.375 | 0.75 | 3 | 1.5 | 0.75 |
| | monitor patient | | | | |
| 4 | 0.5 | 1.0 | 4 | 2.0 | 1.0 |
| 5 | 0.75 | 1.5 | 5 | 3.0 | 2.0 |
| 6 | 1.0 | 2.0 | 6 | 4.5 | 4.0 |
| 7 | 1.25 | 2.5 | 7 | 6.0 | 6.0 |
| 8 | 1.5 | 3.0 | | | 10.0 |
| 9 | 1.75 | 3.5 | | | 15.0 |
| 10 | 2.0 | 4.0 | | | 20.0 |
| | monitor patient | | | | |
| 11 | 2.5 | 5.0 | | | 25.0 |
| 12 | 3.0 | 7.5 | | | 30.0 |
| 13 | 4.0 | 10.0 | | | |
| | monitor patient | | | | |
| 14 | 5.0 | 12.5 | | | |
| 15 | 6.0 | 15 | | | |
| | monitor patient | | | | |
| 16 | | 17.5 | | | |
| 17 | | 20.0 | | | |
| 18 | | 24.0 | | | |

In the case of pramipexole, the effective dose is usually between about 0.125 mg qhs to about 15.0 mg qhs. More usually, the effective dose is between about 0.25 mg qhs and about 6.0 mg qhs. When using ropinirole, the effective dose is usually between about 0.75 mg qhs to about 30.0 mg qhs. More usually, the effective dose is between about 1.5 mg qhs and about 20.0 mg qhs. In either case the daily dose can be divided into multiple dosages forms administered two or more times per day if desirable.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of fibromyalgia. In general the dosage of a compound of the present invention should be increased gradually from a starting dose of about 0.125 mg of compound per day and then increased every 1–7 days to a maximum dose per day of about 30.0 mg of compound per day. Providing patients do not experience intolerable side effects, the dosage should be titrated to achieve a maximal therapeutic effect. The exact optimal dosage for treatment of fibromyalgia with each of the dopamine $D_2/D_3$ agonist compounds will vary depending upon which agonist is being used. Further, the determination of an optimal dopamine $D_2/D_3$ agonist dosage requires only routine testing regimes similar to those disclosed herein.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1/3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Because of their ease in administration, tablets and capsules represent the most advantageous oral dosage unit form, in which case solid pharmaceutical carriers are obviously employed. Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., diluents, granulating agents, lubricants, binders, disintegrating agents and the like. In the case of capsules, tablets, and pills, the dosage forms may also comprise buffering agents. Tablets and pills can additionally be prepared with sugar or enteric coatings, as is known in the art.

2-Amino-6-n-propylamino-4,5,6,7-tetrahydrobenzothiazole is currently available from Pharmacia & Upjohn under the trademark MIRAPEX® in a tablet form for oral administration in tablets containing 0.125 mg, 0.25 mg, 1.0 mg, 1.25 mg or 1.5 mg of (S)-2-amino-4,5,6,7-tetrahydro-6-(propylamino)benzo-thiazole dihydrochloride monohydrate. The tablets contain the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

4-[2-(dipropylamino)-ethyl]-1,3-dihydro-2H-indol-2-one mono hydrochloride is currently available from Smith Kline Beecham under the trademark Requip® in a tablet form for oral administration in tablets containing 0.25 mg, 0.5 mg, 1.0 mg or 2.0 mg or 5.0 mg of 4-[2-(dipropylamino)-ethyl]-1,3,dihydro-2H-indole-2-one monohydrochloride. The tablets contain the following inactive ingredients: croscarmellose sodium, hydrous lactose, magnesium stearate microcrystalline cellulose, and one or more of the following: FD&C Blue No.2 aluminum lake, hydroxypropyl methylcellulose, iron oxides, polyethylene glycol, polysorbate 80, talc, and titanium dioxide.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The present compositions in liposome form can contain, in addition a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W. (1976), p.33 et seq.

While the compounds of the invention can be administered as the sole active pharmaceutical agent, they can also be used in combination with one or more other agents used in the treatment of fibromyalgia. Representative agents useful in combination with the compounds of the invention for the treatment of fibromyalgia include, for example, serotonin uptake inhibitors, mood stabilizing drugs, and the like.

EXAMPLE 1

Patients diagnosed as suffering from fibromyalgia were treated with primapexole, a Parkinson's disease dopamine $D_2/D_3$ receptor agonist. It was hypothesized that dopamine $D_2/D_3$ receptor agonists might suppress hyperadrenergic stimuli and thereby facilitate improved deep, restorative sleep (stage 4) in patients suffering from fibromyalgia. An open label experimental trial of Mirapex® (pramipexole) was conducted with patients initially meeting criteria for fibromyalgia to determine if improved sleep might help alleviate fibromyalgia symptoms. The study included 166 consecutive patients (157-F, 9-M) who had been only partially responsive to previous multiple medications (mean 6.4) and had seen multiple physicians (mean 5.7) in their search for effective treatment. The tolerance, safety profile and patient response to primapexole was assessed over an about 2–12 (mean 4) month period. Pain score [½ point (trace), 1+(classic tenderness), 2+(severe), 3+(exquisite)] for 18 classic tender points (max. 54) was noted before and after increasing the primapexole dosage from 0.125mg qhs up to 6.0 mg qhs slowly over 8 weeks.

Intolerance (n=39, 22%) correlated with psychiatric care (p<0.001) but not quite with increasing age (p=0.54), and not with disability or pretreatment pain score 24.5 (intolerant) vs. 24.6 (tolerant). Median discontinuation of primapexole by primapexole intolerant patients was in 7 days (8.4% paradoxical stimulatory response, 4.8% nausea, 3.0% headache, 1.8% groggy, 1.8% psychiatry, 1.8% dizzy, 1.2% sicca, 0.6% hives, and 0.6% back pain). For those who tolerated primapexole (n=129), mean pain score decreased from 24.5 to 11.4 with a mean dose of 1.55 mg qhs while 29% were pain free, 43.4% were well (score α4), 76% improved 1–47 pain points (mean 18), 20% were unchanged and 3.8% were worse. Lack of improvement correlated with psychiatric care (p<0.001) and disability (p<0.001) in all patients (n=166), but not with age, gender or pretreatment pain score. Table 2 presents a summary of the percent change in pain symptoms observed in patients undergoing treatment with pramipexole.

TABLE 2

Summary of improvement in pain symptoms upon treatment with pramipexole

| Treatment Groups | Pain Free[1] | Well[2] | Better[3] | Not Better[4] | Worse[5] |
|---|---|---|---|---|---|
| All patients (N = 166) | 23% (38/166) | 34% (56/166) | 61.5% (101/166) | 38.5% (64/166) | 3% (5/166) |
| Drug Tolerant Patients[6] (N = 129) | 29.5% (38/129) | 43.4% (56/129) | 76% (98/129) | 24% (31/129) | 3.8% (5/129) |

[1] Pain points for patient were zero.
[2] Pain points for patient decreased by at least 4 points.
[3] Pain points for patient decreased by at least 1 point.
[4] Pain points for patient did not change.
[5] Pain points for patient increased by at least 1 point.
[6] Patients tolerated treatment with pramipexole for more than seven days.

Patient characteristics are summarized in Table 3.

TABLE 3

Patient Demographics

| | Patients who tolerated Pramipexole treatment: N = 129 | All Patients: N = 166 |
|---|---|---|
| Age, mean and (range) | 47 (21–69) | 48 (21–71) |
| Age of onset, mean and (range) | 35 (5–45) | 36 (5–45) |
| Duration of fibromyalgia (yrs), mean and (range) | 12 (5–40) | 12 (5–45) |
| Gender | 120 female/9 male | 157 female/9 male |
| Disabled | 24 (19%) | 30 (18%) |
| Psychiatric care | 41 (32%) | 71 (43%) |

Co-morbidity are as follows: (estimates): Rheumatoid arthritis (15%), psoriatic arthritis (5%), spondylitis (5%), lupus (3%), disk disease (20%), lumbar facet OA (10%), extremity osteoarthritis (5%), soft tissue injury (15%), cancer (1%), post-traumatic stress disorder (55%), bipolar (12%), anxiety (30%), depression (60%), painful neuropathy (5%), substance abuse (1%), child/spouse abuse (80%).

In addition, the treatment of fibromyalgia with the dopamine receptor $D_2/D_3$ agonist pramipexole has also been conducted while the patient was concurrently use the following medications: antidepressants: trazodone, amitriptyline, doxepin, and nortriptyline; selective serotonin re-uptake inhibitors: Prozac®, Paxil®, Zoloft®, Effexor®, and Celexa®; neuroleptics: Neurontin® and Depakote®; the bipolar compound lithium; the antipsychotic Remeron®; benzodiazepines: Ativan®, Klonopin®, Valium®, Xanax®, Restoril®; hypnotics: Ambien® and Sonata®; muscle relaxants: cyclobenzaprine and carisoprodol; narcotics: darvocet-N®, codeine, hydrocodone, oxycodone, morphine, and fentanyl; herbals: valerian root, melatonin, kava kava, picnolgenol, coQ10 and magnesium; and all non-steroidal anti-inflammatory drugs. No drug interactions have been observed between pramipexole and any of the above noted compounds except, increased somnolence as pramipexole becomes effective.

The results presented in Table 2 show that administration of primapexole to patients diagnosed with fibromyalgia is correlated with a decrease in musculoskeletal pain symptoms as measured by tender point indexes. These results further suggest that fibromyalgia somehow interferes with deep restorative sleep and other treatments that tend to improve the control of sympathetic tone and restlessness which otherwise interfere with sleep may help reduce the refractory pain associated with fibromyalgia.

EXAMPLE 2

Patients diagnosed as suffering from fibromyalgia were treated with 4-[2-(dipropylamino)-ethyl]-1,3,dihydro-2H-inodole-2-one monohydrochloride, a Parkinson's disease dopamine $D_2/D_3$ receptor agonist which is known to suppress hyperadrenergic stimuli and thereby facilitate improved deep, restorative sleep. An open label experimental trial of Requip® (ropinirole) was conducted with patients initially meeting criteria for fibromyalgia to determine if improved sleep might help alleviate fibromyalgia symptoms. The demographics of the patients treated with ropinirole reflected those who did not tolerate treatment with pramipexole.

The study included 14 patients who had been only partially responsive to previous multiple medications such as, for example Sinemet®, Ativan® or Klonopin®. The tolerance, safety profile and patient response to ropinirole was assessed over an about 3–12 (mean 4) month period. Pain score [1/2 point (trace), 1+(classic tenderness), 2+(severe), 3+(exquisite)] for 18 classic tender points (max. 54) was noted before and after increasing the ropinirole dosage from 0.25mg qhs up to 4.0 mg qhs slowly over 8 weeks. Mean pain score decreased from 21.7 to 14.0 with a mean dose of 2.3 mg qhs. About 64% (9/14) of the patients exhibited an improved tender points index, while 28% (4/14) were unchanged and 7% (1/14) were worse.

The above noted results show that administration of ropinirole to patients diagnosed with fibromyalgia is correlated with a decrease in musculoskeletal pain symptoms as measured by tender point indexes.

While various embodiments of the invention have been illustrated and described, it will be appreciated that various changes can be made therein without departing from the spirit and scope of the invention.

What is claimed is:

1. A method for treating fibromyalgia comprising administering to a patient afflicted with such condition a therapeutically effective amount for treating such condition of a non-ergot dopamine $D_2/D_3$ receptor agonist or a pharmacologically acceptable acid addition salt thereof, alone or in association with a pharmaceutically acceptable carrier, wherein the dopamine $D_2/D_3$ receptor agonist is a tetrahydro-benzthiazole compound of formula I:

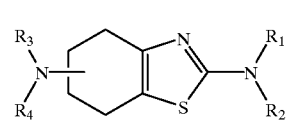

(I)

wherein:
  $R_1$ represents a hydrogen atom, a $C_{1-6}$ alkyl group, a $C_{3-6}$ alkenyl, a $C_{3-6}$ alkynyl, a $C_{1-6}$ alkanoyl group, a phenyl $C_{1-3}$ alkyl group, or a phenyl $C_{1-3}$ alkanoyl group, wherein the phenyl nuclei may be substituted by 1 or 2 halogen atoms;
  $R_2$ represents a hydrogen atom or a $C_{1-4}$ alkyl group;
  $R_3$ represents a hydrogen atom, a $C_{1-7}$ alkyl group, a $C_{3-7}$ cycloalkyl group, a $C_{3-6}$ alkenyl group, a $C_{3-6}$ alkynyl group, a $C_{1-7}$ alkanoyl group, a phenyl $C_{1-3}$ alkyl, or a phenyl $C_{1-3}$ alkanoyl group, wherein the phenyl nucleus may be substituted by fluorine, chlorine or bromine atoms; and
  $R_4$ represents a hydrogen atom, a $C_{1-4}$ alkyl group, a $C_{3-6}$ alkenyl group, or a $C_{3-6}$ alkynyl group; or R₃ and R₄ together with the nitrogen atom between them represent a pyrrolidino, piperidino, hexamethyleneimino or morpholino group.

2. A method accordidng to claim 1, wherein the therapeutically effective amount is of from about 0.1 to 50.0 mg/day.

3. A method accordidng to claim 1, wherein the therapeutically effective amount is of from about 0.25 to 40.0 mg/day.

4. A method according to claim 1, wherein the compound of formula I is 2-amino-6-n-propylamino-4,5,6,7 tetrahydrobenzothiozole or the (-)-enantiomers thereof.

5. A method according to claim 1, wherein the therapeutically effective amount is of from about 0.5 to about 20.0 mg/day.

* * * * *

UNITED STATES PATENT AND TRADEMARK OFFICE
CERTIFICATE OF CORRECTION

PATENT NO. : 6,277,875 B1
DATED : August 21, 2001
INVENTOR(S) : A.J. Holman

It is certified that error appears in the above-identified patent and that said Letters Patent is hereby corrected as shown below:

<u>Title page,</u>
Item [57], ABSTRACT, "metho s" should read -- methods --

<u>Column 15,</u>
Line 4, "accordidng" should read -- according --
Line 7, "accordidng" should read -- according --

Signed and Sealed this

Sixteenth Day of April, 2002

Attest:

JAMES E. ROGAN
*Director of the United States Patent and Trademark Office*

*Attesting Officer*